United States Patent [19]

Garlaschelli et al.

[11] Patent Number: 4,771,063
[45] Date of Patent: Sep. 13, 1988

[54] FUNGICIDALLY ACTIVE N-(2-METHYL-5-CHLOROPHENYL)-N-METHOXYACETYL-3-AMINO-1,3-OXAZOLIDIN-2-ONE

[75] Inventors: Luigi Garlaschelli, Pavia; Franco Gozzo; Luigi Mirenna, both of Milan, all of Italy

[73] Assignee: Montedison S.p.A, Milan, Italy

[21] Appl. No.: 82,939

[22] Filed: Aug. 5, 1987

Related U.S. Application Data

[60] Continuation of Ser. No. 742,004, Jun. 6, 1985, abandoned, which is a division of Ser. No. 498,966, May 27, 1983, abandoned, which is a continuation-in-part of Ser. No. 185,248, Sep. 5, 1980, abandoned, and a continuation-in-part of Ser. No. 348,426, Feb. 2, 1982, abandoned, and a continuation-in-part of Ser. No. 435,366, Oct. 20, 1982, abandoned.

[51] Int. Cl.$^4$ ............... C07D 263/08; A01N 43/76
[52] U.S. Cl. .................................. 514/376; 548/230; 564/211; 564/310

[58] Field of Search .................... 514/376; 548/230

[56] References Cited

U.S. PATENT DOCUMENTS 4,457,937  7/1984  Sandmeier et al. ............... 514/376
4,477,461  10/1984  Garlaschelli et al. ............. 514/376

FOREIGN PATENT DOCUMENTS 2499568  8/1982  France .
2058071  4/1981  United Kingdom ............ 548/230

Primary Examiner—Donald G. Daus
Assistant Examiner—E. Bernhardt
Attorney, Agent, or Firm—Stevens, Davis, Miller & Mosher

[57] ABSTRACT

New fungicides which are N-aryl-N-acyl-3-amino-oxazolidin-2-ones and use thereof in fighting infections of useful plants by fungi are disclosed. The compounds of the invention have a high fungicidal activity combined with a good compatibility with the plants to be defended against attack by fungi.

5 Claims, No Drawings

FUNGICIDALLY ACTIVE N-(2-METHYL-5-CHLOROPHENYL)-N-METHOXYACETYL-3-AMINO-1,3-OXAZOLIDIN-2-ONE

This application is a continuation of application Ser. No. 742,004, filed June 6, 1985, which in turn is a divisional of application Ser. No. 498,966, filed May 27, 1983, which in turn is a continuation-in-part of application Ser. No. 185,248, filed Sept. 5, 1980, and Ser. No. 348,426, filed Feb. 2, 1982, and Ser. No. 435,366, filed Oct. 20, 1982, all now abandoned.

BACKGROUND OF THE INVENTION

Fungicidal compounds of the class of N-phenyl-1,3-oxazolidin-2,4-diones are described in, for instance, Dutch Patent Application No. 68,17249 (Sumitomo), in French Pat. No. 2,172,295 (BASF), and in Belgian Pat. No. 874,406 (Montedison S.p.A.).

Recently, there has also been described the bactericidal and fungicidal activity of some derivatives of aniline and glycine which carry on the nitrogen atom a variously substituted phenyl group and an acylic group of varying nature.

More particularly, this acylic group may consist of an α- or β-haloalkanoyl (German Patent Applicaton No. DOS 2,513,789—Ciba-Geigy), or of an acetyl group substituted in α-position with a sulphur or oxygen atom in its turn bound to groups of varying nature (French Patent Application No. 7,510,722—Ciba Geigy) or again of a 2-furoyl, 2-thienoyl or pyridyl-2-carbonyl group (German Patent Application Nos. DOS 2,513,732 and 2,513,788—Ciba Geigy). Likewise, there has been described the microbicidal activity of methylalaninates carrying on the nitrogen atom a 2,6-dialkyl-phenyl and one of the following groups; cyclopropanyl, acryloyl, crotonyl (Swiss Patent Applications Nos. 4,988/74 and 2,906/75).

Other derivatives of fungicidal acyl-anilines have recently been described in Belgian Pat. No. 863,615 (Ciba-Geigy) and in German Patent Application No. DOS 2,745,633 (Chevron).

The interest in the search for new derivatives from acyl-anilines having fungicidal action originates from the exigency of finding acylaniline derivatives that will have a high fungicidal activity combined with a lack of phytotoxicity.

In fact, some of the already known products, although developing an excellent fungicidal activity, prove, however, to be also toxic for the plants that one wishes to protect against infections by fungi.

The damages caused by the phytotoxicity to the plants to be protected can hardly be avoided by using a dose of a fungicidal compound that may be the best compromise between the fungicidal activity of the compound and its phytotoxicity.

In fact, in the practical application in agricultural cultivations, the quantity of product that actually remains on the plant varies considerably depending on various factors such as, for instance, the weather conditions, (particularly the frequency of rainfalls), and the correctness and frequency of the applications carried out by the farmer.

THE PRESENT INVENTION

One object of this invention is to provide new oxazolidin-2-ones which are highly active fungicides and safe for use in fighting fungi infestations of useful plants without damage to the plants, even when used in large quantities.

This and other objects, including use of the fungicides, are achieved by the present invention which provides compounds corresponding to the general formula:

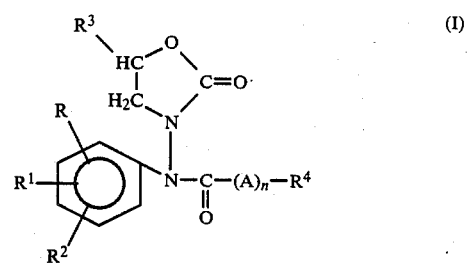

wherein
R, $R^1$ and $R^2$, equal to or different from each other, are H, halogen, alkyl $C_1$–$C_4$ or alkoxyl $C_1$–$C_4$, at least one of the positions 2 and 6 on the phenyl ring being unsubstituted;
$R^3$ is H or $CH_3$;
A is —$CH_2$— or

n is 0 or 1; and
R is H, alkyl $C_1$–$C_5$ optionally substituted with halogen atoms; cycloalkyl $C_3$–$C_6$; alkenyl $C_2$–$C_5$; ethinyl; halogen or CN (when n=1); phenyl optionally substituted with alkyls $C_1$–$C_5$ or with halogen atoms; heterocyclic group with 5 to 6 members containing from 1 to 3 hetero-atoms (in particular: furyl, tetrahydrofuryl, thienyl, pyrimidyl, pyridyl, imidazolyl, pyrazolyl, triazolyl); acetyl; COO-alkyl; —$OR^5$; —$SR^5$;

with $R^5$ and $R^6$ (equal to or different from each other) being H; alkyl $C_1$–$C_5$; alkenyl $C_2$–$C_5$; phenyl; a heterocyclic group of 5 or 6 terms containing from 1 to 3 hetero-atoms; $SO_2$-alkyl; or acetyl): and which are endowed with very effective fungicide activity while having a very low phytotoxicity.

Only one of the compounds close to the scope of general formula (I) is known in the literatue. More particularly, said compound is N-phenyl-N-acetyl-3-amino-oxazolidin-2-one of formula (II):

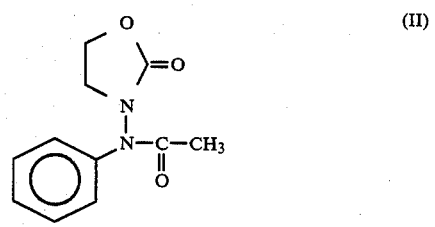

which has been described in the "Journal of Organic Chemistry", 31, p. 968 (1966).

The compound of formula (II) had not been recognized, however, as possessing fungicidal activity.

The preparation of the compounds of general formula (I) is carried out by means of processes known in the normal practice of organic chemistry.

For instance, an arylhydrazine (3) may be prepared by reacting the corresponding aniline (1) with sodium nitrite (NaNO$_2$) in hydrochloric acid, and by then reducing the diazonium salt (2) thus obtained (scheme 1, equation 1 below), as described for instance in "Journal of American Chemical Society", 81, p. 4673 (1959).

The aryl-hydrazine is then caused to react with 2-halo-ethyl or 1-methyl-2-haloethyl-chloroformate (4) (in its turn prepared by the action of phosgene on a halohydrin) in the presence of a base, and the intermediate (5) thus obtained is then cyclized in the presence of bases, thereby obtaining intermediate (6) (scheme 1, equation 2). This process has been described in the "Journal of American Chemical Society", 48, 1951 (1926).

Intermediate (6) is then condensed by means of the proper acylic halide (7), according to known techniques (scheme 1, equation 3). The condensation reaction between intermediate (6) and acylic halide (7) may be substituted or replaced by analogous reactions known in the literature, which allow the introduction of particular acylic groups. For instance, the compounds of general formula (I), in which in the acylic part:

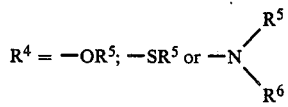

may be prepared by reacting intermediate (6) with phosgene or with haloacetyl or halopropionyl halides (such as, for instance,

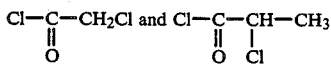

respectively) and by then substituting the halogen atom according to known techniques.

The compounds of formula (I), in which the acylic part is

and where R$^4$ is NHR$^5$, may be prepared by reacting intermediate (6) with an isocyanate of the formula: R$^5$—N=C=O.

The compounds of formula (I), in which the acylic part is

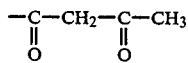

(A=CH$_2$; R$^4$=acetyl), may be prepared by reacting the intermediate (6) with diketene.

Scheme 1

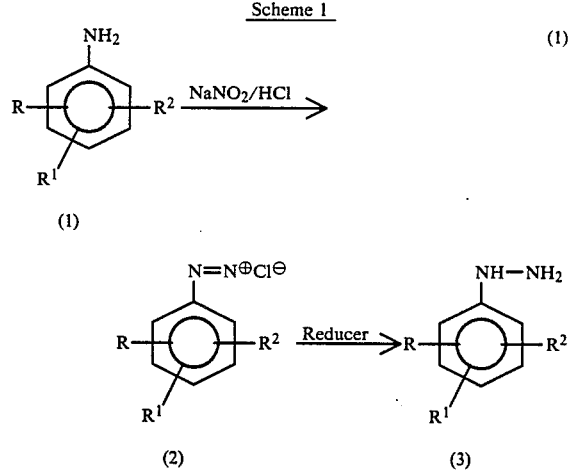

[X=halogen; R, R$^1$, R$^2$, R$^3$, R$^4$, A and n have the same meanings as in general formula (I)]. Reaction 3 is carried out in an inert solvent, in the presence of a halogenhydric acid-accepting base, at reflux temperature.

The compounds of general formula (I) are endowed with an excellent fungicide activity against phytopathogenous fungi and their action has both a preventive character (i.e., they hinder the inception of the disease), as well as a curative character (when, that is, the infection is already in progress).

The most important class of phytopathogenous fungi which can be fought by using the compounds of the invention, is that of Phycomicetes which comprises Plasmopara spp., Phytophtora spp., Peronospora spp., Pseudoperonospora spp. and Phythium spp.

The fungicidal compounds of the invention are effective for fighting fungi infections of useful plants such as vine, tomato, tobacco, potato and other cultivations.

They possess good systemic characteristics (i.e., they are carried into the various parts of the plant) wherefore it is possible to apply these products both on the leaves as well as on the soil.

Moreover, the compounds of this invention proved to be compatible with the plants that are to be protected against fungi attacks.

The majority of the compounds of the invention do not show any sign of phytotoxicity at the amounts tested, while the remainder showed only a low phytotoxicity, lower, at any rate, than that of other known fungicides.

In practical agricultural applications, the compounds of the invention can be used as such or in form of suitable compositions, consisting of the compounds of the invention as active principle, solid or liquid inert carriers and, optionally, surfactants and other additives. If desired, active compounds, such as other fungicides, insecticides, plant-growth regulators and so on, may be present in the compositions.

The compounds may be formulated according to the normal agricultural practice, as dusts, powders, wettable powders, emulsifiable liquids, granular formulates and so on.

The amounts of the compounds of the invention to be distributed for fighting infections by fungi depends on various factors, such as the active compound used, the type of composition or formulation, the kind of infection and its degree, the kind of agricultural cultivation to be protected from fungi attack, the climatic and weather conditions, and so on.

Generally, amounts comprised between 10 and 500 g/ha are sufficient, the preferred amount being from 100 to 250 g/ha.

The following examples are given to illustrate the invention in more detail, and are not intended to be limiting.

EXAMPLE 1

Preparation of N-(2-methyl-5-chlorophenyl)-N-(methoxyacetyl)-3-amino-1,3-oxazolidin-2-one (Compound No. 23)

(A) Preparation of 2-methyl-5-chloro-phenylhydrazine 125 g of 2-methyl-5-chloro-aniline were dripped into a solution of 220 ml of concentrated HCl in 150 ml of water. After cooling down to −5° C., this mixture was thereupon additioned with a solution of 66 g of NaNO$_2$ in 150 ml of H$_2$O, over a period of time of about 1 hour and under vigorous stirring.

To the yellow-orange colored suspension thus obtained were added, at 0° C. and in about 4 hours, 450 g of SnCl$_2$.2H$_2$O in 600 ml of a 5N aqueous solution of HCl.

The mixture was then maintained under stirring for 24 hours, allowing the temperature to rise up to +20° C. The solid thus formed was filtered, dissolved in 700 ml of H$_2$O and then treated with a solution of 230 g of NaOH in 300 ml of H$_2$O, at a temperature of between 10° and 15° C., after which the product was extracted with diethylether (3×250 ml).

The etheric extract, after washing with H$_2$O and anhydrification on Na$_2$SO$_4$, was brought up to a volume of 1500 ml with diethylether and then was treated with anhydrous gaseous HCl, until attaining the complete precipitation of the chlorohydrate of 2-methyl-5-chloro-phenylhydrazine.

The salt was then filtered and dried, thereby obtaining 48 g of a white solid having a melting point (m.p.) equal to 210°-212° C. with decomposition.

By treatment with NaOH, from the chlorohydrate was obtained 2-methyl-5-chloro-phenylhydrazine.

(B) Preparation of 3-(2-methyl-5-chloroaniline)oxazolidin-2-one

To 32 g of 2-chloroethyl-chloroformate, prepared from phosgene and ethylenic chlorohydrine, in 200 ml of benzene, there were additioned, at 10° C., the following reactants: 42 g of 2-methyl-5-chloro-phenylhydrazine (see point A), and 18 g of pyridine in 100 ml of benzene. This addition once completed, the temperature was allowed to rise up to 20° C. under constant vigorous stirring.

The pyridine chlorohydrate was removed by washing with water. The benzenic solution was further washed with HCl and with water to a neutral pH, and was then dried on Na$_2$SO$_4$ and evaporated to yield 58 g of an oily product which, crystallized from ligroin, gave 42 g of a light colored solid having a m.p. of 62°-63° C., and which consisted of 1-(2-methyl-5-chlorophenyl)-2-(β-chloroethyl)-oxycarbonyl hydrazine. [The IR spectroscopy gave: $\nu$ (C=O)=1690-1725 cm$^{-1}$; $\nu$ (NH—CO)=3230 cm$^{-1}$; $\nu$ (NH—Ar)=3330 cm$^{-1}$].

37 g of this intermediate were dissolved in 500 ml of toluene and the solution was treated with 16 g of tetramethylguanidine. This mixture was reflux-heated for 3 hours under stirring. After cooling down, the mixture was washed with 200 ml of H$_2$O and then with 100 ml of diluted HCl and finally again with 200 ml of H$_2$O.

The aqueous phases, reunited, were extracted with CH$_2$Cl$_2$(2×200 ml).

The combined organic phases were anhydrified on Na$_2$SO$_4$ and then the solvent was evaporated, thereby obtaining a solid residue which was crystallized from ligroin-ethylacetate (2:1).

There were thus obtained 26 g of 3-(2-methyl-5-chloroaniline)-oxazolidin-2-one having a m.p. of 165°-166° C. [The IR spectrum showed: $\nu$(C=O)=1750 cm$^{-1}$; $\nu$(NH)=3330 cm$^{-1}$].

The cyclization reaction was repeated, dissolving the intermediate with m.p. of 62°-63° C. in ethanol containing sodium ethylate, and by then reflux-heating the solution. After an analogous treatment of the reaction mixture, the same intermediate was isolated; it had a m.p. of 165°-166° C.

(C)

To 2.2 g of the intermediate, prepared as described in (B), in 70 ml of toluene and 0.2 ml of dimethylformamide, there were added 1.1 g of methoxyacetyl chloride. The reaction mixture was then reflux-heated for 8 hours. After cooling down, the reaction mixture was subjected to complete evaporation of the solvents to yield 3.2 g of a thick oil. Crystallization of a sample of this oil from ethyl acetate—ligroin (1:2) gave a solid melting at 69°-71° C. while crystallization from isopropanol afforded a solid melting at 76°-77° C.

Infra-red and $^1$H-NMR spectra of these solid products are identical.

IR (nujol) main bands at: 2930, 1775, 1710, 1490, 1410, 1130 and 1035 cm$^{-1}$.

$^1$H-NMR (CDCl$_3$, TMS): δ(ppm) 2.24, 2.40 (s, s, 3H, CH$_3$-φ); 3.38, 3.53 (s, s, 3H, CH$_3$-O); 3.6-4.0 (m, 6H); 7.2-7.8 (m, 3H, aromatic protons); (s=singlet, m=multiplet or complex signal).

EXAMPLE 2

Operating analogously to Example 1, there were prepared the other compounds reported in the following Table 1:

TABLE 1[a]

| Compound No. | R | R$^1$ | R$^2$ | R$^3$ | n | A | R$^4$ | m.p.[b] (°C.) | IR[c] (cm$^{-1}$) |
|---|---|---|---|---|---|---|---|---|---|
| 1 | H | H | H | H | 1 | CH$_2$ | Cl | 71-4 | 1690-1760 |
| 2 | H | H | H | H | 1 | CH$_2$ | C$_6$H$_5$ | 112-4 | 1680-1760 |
| 3 | H | H | H | H | 1 | CH$_2$ | i.C$_3$H$_7$ | oil | 1680-1770 |
| 4 | H | H | H | H | 1 | CH$_2$ | OCH$_3$ | 86-91 | 1690-1760 |

Notes to Table 1:
[a]The elemental analysis of all the compounds is consistent with the assigned structure.
[b]Melting points have not been corrected.
[c]Only the bands corresponding to $\nu$C=O are reported.

EXAMPLE 3

Curative activity on vine Peronospora (*Plasmopara viticola* (B et C) Berl et de Toni)

Vine leaves of Cv. Dolcetto, grown in pots in a conditioned environment stabilized at 25° C. and 60% of relative humidity, were sprinkled on the lower faces thereof with an aqueous suspension of *Plasmopara viticola* conidia (200,000 conidia/cc). After 24 hours of dwelling in a humidity (moisture) saturated environment, stabilized at 21° C., the plants were treated by sprinkling both faces of the leaves with the products under examination in a hydroacetone solution at 20% of acetone (vol./vol.).

At the end of the incubation period (7 days), the degree of infection was assessed by sight on the basis of a value scale with indexes going from:

0: no control, infection equal to that of witness plant (infected but non-treated plants)
1: 1–20% reduction of the infection;
2: 20–60% reduction of the infection;
3: 60–90% reduction of the infection;
4: reduction of the infection greater than 90%.

The results obtained are recorded in the following Table 2:

TABLE 2

Curative activity against vine Peronospora by foliar application at the dose of 0.5%.

| Compound No. | Activity |
|---|---|
| 1 | 3 |
| 2 | 3 |
| 3 | 4 |
| 4 | 4 |

EXAMPLE 4

Determination of the phytotoxicity degree

Leaves of Cv. Dolcetto vine plants, grown in pots in a conditioned environment stabilized at 25° C. and at 60% relative humidity, were treated by sprinkling both leaf faces with a hydroacetone solution at 20% of acetone (vol./vol.) of the products under examination.

After 7 days, the extent or degree of phytotoxic symptoms were evaluated by sight according to a value scale with indexes ranging from 100 (for fully damaged plant) to 0 (for a healthy plant).

The corresponding data are recorded in Table 3, in comparison with the phytotoxicity indexes of the two compounds known to be shortly marketed, i.e.: "Furalaxyl" (British Pat. No. 1,448,810—Ciba-Geigy) and "Ridomil" (French Patent Application No. 2,267,042—Ciba-Geigy).

TABLE 3

| Phytotoxicity index for doses at 0.6%‰ | |
|---|---|
| Compound No. | Phytotoxicity index |
| 1 | 0 |
| 3 | 10 |
| "Furalaxyl"[1] | 100 |

TABLE 3-continued

| Phytotoxicity index for doses at 0.6%‰ | |
|---|---|
| Compound No. | Phytotoxicity index |
| "Ridomil"[2] | 60 |

[1]"Furalaxyl" = N—(2,6-dimethylphenyl)-N—(1'-carbomethoxy-ethyl)-2-furoylamide:

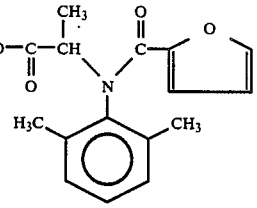

[2]"Ridomil" = N—(2,6-dimethylphenyl)-N—(1'-carbomethoxy-ethyl)-methoxyacetamide:

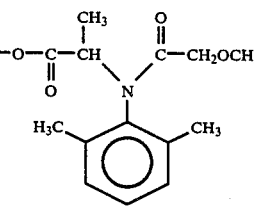

EXAMPLE 5

Preparation of N-(methoxyacetyl)-N-(3-chlorophenyl)-3-aminooxazolidin-2-one (A) Preparation of 2-chloroethyl 3-(3-chlorophenyl-carbazate)

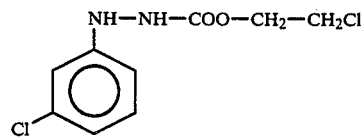

A solution of NaOH (1.6 g) in water (20 ml) was added dropwise in 1 hour to a mixture stirred at 5°–10° C. of
3-chloro-phenylhydrazine hydrochloride (3.6 g);
water (6 ml);
methylene chloride (20 ml);
2-chloroethyl chloroforminate

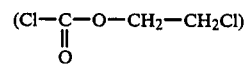

(2–9 g).

Once the addition was completed the mixture was further stirred for 1 hour at 20° C.

Thereupon the organic phase was separated and dried on anhydrous Na$_2$SO$_4$ and filtered. The solvent was then removed by evaporation at reduced pressure thereby obtaining 5 g of a yellowish solid which crystallized from diisopropyl ether afforded 3 g of the desired product (white solid, m.p.=92°–93° C.).

(B) Preparation of 3-(3-chlorophenyl)-amino-oxazolidin-2-one

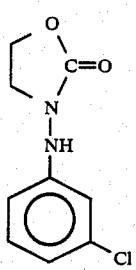

A solution of the carbazate prepared as described in point (A) (10 g) in toluene (120 ml) was additioned with tetramethylquanidine (4 g) and the mixture was reflux-heated for 3 hours under stirring.

After cooling down the mixture was washed with water (50 ml), diluted hydrochloric acid (25 ml) and finally with water (50 ml).

The aqueous phases, reunited, were extracted with $CH_2Cl$ (2×50 ml). The combined organic phases were dried on anhydrous $Na_2SO_4$ and filtered. The solvent was removed by evaporation at reduced pressure thereby obtaining the desired product [IR: 1770 cm$^{-1}$ ($\nu CO$) 3340 cm$^{-1}$ ($\nu NH$)].

(C) Preparation of N-(methoxyacetyl)-N-3-chlorophenyl)-3-amino-oxazolidin-2-one

Methoxyacetyl chloride (2.5 g) was added dropwise to a stirred solution of the intermediate prepared as described in point (B) (5 g) and pyridine (1.7 g) in $CH_2Cl_2$ (40 ml).

The mixture was then stirred at room temperature for 30 minutes and at 40° C. for 2 hours.

After cooling down to room temperature the mixture was washed with aqueous $H_2SO_4$ at 5% concentration (30 ml), dried on anhydrous $Na_2SO_4$ and filtered.

The solvent was removed by evaporation at reduced pressure thereby obtaining 2.8 g of a yellow oil which was then purified by chromatography on a silica gel column (eluent hexane-ethyl acetate in the ratio 1:1) thus affording 2.5 g of the desired product (white solid, m.p.=76°-8° C.) whose characteristics are reported in Table 4.

EXAMPLE 6

By operating according to the procedure described in Example 5 and starting from the appropriate hydrazine-derivative, the compounds reported in the following Table 4 have been prepared.

TABLE 4 compounds of formula$^{(a)}$:

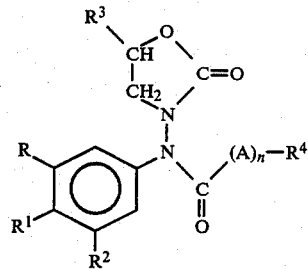

| Compound No. | R | $R^1$ | $R^2$ | $R^3$ | n | A | $R^{4(b)}$ | m.p.$^{(c)}$ (°C.) | IR$^{(d)}$ (cm$^{-1}$) |
|---|---|---|---|---|---|---|---|---|---|
| 5 | Cl | H | H | H | 1 | $CH_2$ | $OCH_3$ | 76-8 | 1710-1775 |
| 6 | Cl | H | H | H | 0 | — | ▷ | oil | 1680-1775 |
| 7 | Cl | H | H | H | 1 | $CH_2$ | Cl | 101-3 | 1710-1775 |
| 8 | Cl | H | Cl | H | 0 | — | ▷ | oil | 1690-1775 |
| 9 | H | Cl | H | H | 0 | — | ▷ | oil | 1685-1775 |
| 10 | Cl | Cl | H | H | 0 | — | ▷ | oil | 1685-1775 |
| 11 | Cl | H | H | H | 1 | $CH_2$ | $C_6H_5$ | oil | 1690-1775 |
| 12 | $CH_3$ | H | H | H | 1 | $CH_2$ | $OCH_3$ | 84-6 | 1705-1775 |
| 13 | Cl | H | Cl | H | 1 | $CH_2$ | $OCH_3$ | 90-1 | 1720-1765 |
| 14 | H | $CH_3$ | H | H | 1 | $CH_2$ | $OCH_3$ | 110-1 | 1710-1760 |
| 15 | Cl | H | H | H | 1 | $CH_2$ | $i.C_3H_7$ | 106-8 | 1690-1760 |
| 16 | Cl | Cl | H | H | 1 | $CH_2$ | $OCH_3$ | oil | 1710-1770 |
| 17 | F | H | H | H | 1 | $CH_2$ | $OCH_3$ | 92-4 | 1710-1765 |
| 18 | H | Cl | H | H | 1 | $CH_2$ | $OCH_3$ | 100-2 | 1730-1760 |
| 19 | Cl | H | H | H | 0 | — | $CHCl_2$ | oil | 1710-1775 |
| 20 | H | $OCH_3$ | H | H | 1 | $CH_2$ | $OCH_3$ | oil | 1700-1775 |
| 21 | Cl | H | H | H | 0 | — | $CH_2-CH_2Cl$ | oil | 1725-1775 |

TABLE 4-continued compounds of formula[a]:

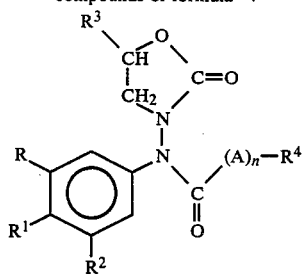

| Compound No. | R | R$^1$ | R$^2$ | R$^3$ | n | A | R$^{4[b]}$ | m.p.[c] (°C.) | IR[d] (cm$^{-1}$) |
|---|---|---|---|---|---|---|---|---|---|
| 22 | Cl | H | Cl | H | 1 | CH$_2$ | OCH$_3$ | oil | 1720–1765 |

Notes to Table 4
[a]The elemental analysis of all the compounds is consistent with the assigned structure

[b] ◁ = cyclopropyl

[c]melting points have not been corrected

[d]only the bands corresponding to νC═O are reported

EXAMPLE 7

Curative activity on vine Peronospora (*Plasmopara viticola* (B et C) Berl et de Toni)

Vine leaves of Cv. Dolcetto, grown in pots in a conditioned environment stabilized at 25° C. and 60% of relative humidity, were sprinkled on the lower faces thereof with an aqueous suspension of *Plasmopara viticola* conidia (200,000 conidia/cc). After 24 hours of dwelling in a humidity (moisture) saturated environment, stabilized at 21° C., the plants were treated by sprinkling both faces of the leaves with the products under examination in a hydroacetone solution at 20% of acetone (vol./vol.).

At the end of the incubation period (7 days), the degree of infection was assesssed by sight on the basis of a value scale with indexes going from:
- 0: no control, infection equal to that of witness plant (infected but non-treated plants)
- 1: 1–20% reduction of the infection;
- 2: 20–60% reduction of the infection;
- 3: 60–90% reduction of the infection;
- 4: reduction of the infection greater than 90%.

The results obtained are recorded in the following Table 5.

TABLE 5

Curative activity against vine Peronospora by foliar application at the dose of 0.5%.

| COMPOUND NO. | ACTIVITY |
|---|---|
| 5 | 4 |
| 7 | 4 |
| 12 | 4 |
| 13 | 4 |
| 15 | 4 |
| 17 | 4 |
| 19 | 4 |

EXAMPLE 8

Curative activity on Peronospora of tobacco (*Peronospora tabacina* Adam)

The leaves of tobacco plants Cv. Burley, grown in pots in a conditioned environment, were sprinkled, on the lower faces of the leaves, with a *Peronospora tabacina* conidia-suspension (200,000 conidia/cc). After 6 hours of dwelling in a humidity saturated environment, the plants were transferred to a conditioned environment stabilized at 20° C. and 70% of relative humidity, for the incubation of the fungus. 24 hours after the infection, treatment was carried out by sprinkling both leaf faces with the product under examination, in a hydroacetone solution of 20% in acetone (vol./vol.).

At the end of the incubation period (6 days) the extent of the infection was assessed by sight according to a value scale with an index range equal to that of Example 7.

TABLE 6

Curative activity by foliar application at doses of 0.5%. on plants infected with Peronospora of Tobacco

| COMPOUND NO. | ACTIVITY |
|---|---|
| 5 | 4 |
| 7 | 4 |
| 12 | 4 |
| 13 | 4 |
| 15 | 4 |
| 17 | 4 |
| 19 | 4 |

EXAMPLE 9

Determination of the phytotoxicity degree

Leaves of Cv. Dolcetto vine plants, grown in pots in a conditioned environment stabilized at 25° C. and at 60% relative humidity, were treated by sprinkling both leaf faces with a hydroacetone solution at 20% of acetone (vol./vol.) of the products under examination.

After 7 days, the extent or degree of phytotoxic symptoms were evaluated by sight according to a value scale with indexes ranging from 100 (for fully damaged plant) to 0 (for a healthy plant).

The corresponding data are recorded in Table 7, in comparison with the phytoxicity indexes of the two compounds known to be shortly marketed, i.e.: "Furalaxyl" (British Pat. No. 1,448,810—Ciba-Geigy) and "Ridomil" (French Patent Application No. 2,267,042—Ciba-Geigy).

TABLE 7

| Phytotoxicity index for doses at 0.6%°/₀₀ | |
|---|---|
| COMPOUND NO. | Phytotoxicity index |
| 5 | 10 |
| 12 | 0 |
| 17 | 0 |
| "Furalaxyl"[1] | 100 |
| "Ridomil"[2] | 60 |

[1]"Furalaxyl" = N—(2,6-dimethylphenyl)-N—(1'-carbomethoxy-ethyl)-2-furoyl-amide:

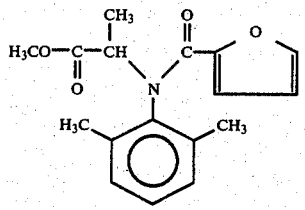

[2]"Ridomil" = N—(2,6-dimethylphenyl)-N—(1'-carbomethoxy-ethyl)-methoxyacetamide:

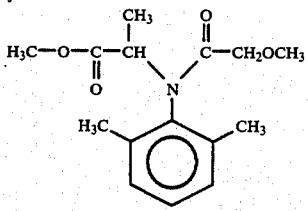

EXAMPLE 10

Among the compounds of the invention, N-(2-methyl-5-chlorophenyl)-N-methoxyacetyl-3-amino-1,3-oxazolidin-2-one (compound 23) is exceptionally active in the fight against fungi infections of useful plants.

Prepared by methods analogous to those described herein, and in Belgian Pat. No. 885,117, starting from 2-methyl-5-chloro-phenylhydrazine, compound 23 occurs in the form of a thick oil showing, at 50° C., a refractive index $n_{50}=1.5375$. On crystallization from ethyl acetate plus ligroin, it is obtained in the form of a white crystalline solid (m.p. 69°–70° C.) and on IR analysis shows the following main absorption bands: 2930, 1775, 1710, 1490, 1410, 1130 and 1135 cm$^{-1}$. It has the formula

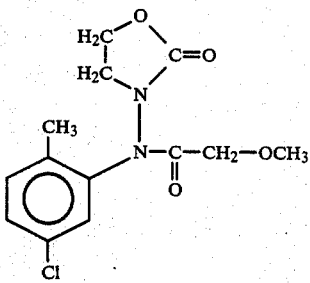

Its preparation is described in details in example 1.

The superior fungicidal activity of N-(2-methyl-5-chlorophenyl)-N-methoxyacetyl-3-amino-1,3-oxazolidin-2-one is apparent from the results of the following tests. Its fungicide activity is surprisingly high in an absolute sense inasmuch as, at extremely low doses (0.0005%) it still shows full activity, i.e., a 100% reduction of the fungus infection.

EXAMPLE 11

Curative activity against *Plasmopara viticola* on vine plants

General methodology:

The leaves of cv. Dolcetto vine plants, grown in pots in a conditioned environment at 25° C. and at 60% relative humidity, were sprinkled on their lower faces with an aqueous suspension of conidia of *Plasmopara viticola* (B. et C.) Berl et de Toni (200,000 conidia/cc).

After a dwelling time of 24 hours, in a humidity-saturated environment at 21° C., the plants were then treated by sprinkling both leaf faces with compound 23 dissolved in a hydroacetonic solution (acetone=20% by volume), respectively after 1, 2 and 3 days from the infection date.

At the completion of the incubation period (7 days), the degree of infection was evaluated according to a value scale ranging from 100 (for a healthy plant) to 0 (for a completely infected plant).

The curative activity of compound 23 against *Plasmopara viticola* on vine is 100% reduction of the fungus infection at the doses, in percent, of 0.01; 0.005; 0.001 and 0.0005.

EXAMPLE 12

Curative action against *Peronospera tabacina* on tobacco plants

General methodology:

Leaves of tobacco plants of cv. Burley, grown in pots in a conditioned environment, were sprinkled on the lower leaf faces with an aqueous suspension of conidia of *Peronospera tabacina* Adam (200,000 conidia/ml).

After a dwell time of 6 hours in a humidity-saturated environment, the tobacco plants were placed in an environment conditioned at 20° C. and 70% relative humidity, for the incubation of the fungus.

After 24 and 48 hours, respectively, from the moment of the infection there was carried out the treatment by sprinkling both leaf faces with compound 23 in a hydroacetonic solution (acetone=20% by volume).

At the end of the incubation period (6 days), the degree of infection was evaluated according to an evaluation scale with values ranging from 100 (for a healthy plant) to 0 (for a completely infected plant).

The curative action of compound 23 against *Peronospera tabacina* on tobacco plant leaves is 100% reduction of the fungus infection at doses, in percent, of 0.01; 0.005; 0.001 and 0.0005.

EXAMPLE 13

Preventive action against *Plasmopara viticola* on vine

General methodology:

The vine leaves of cv. Dolcetto, grown in pots in a conditioned environment, were sprinkled on the upper leaf faces with compound 23 dissolved in a hydroacetonic solution at 20% of acetone (vol./vol.).

The plants were then placed in a conditioned environment and sprinkled on their lower leaf faces, respectively after 1 and 7 days from the day of the treatment with compound 23 with an aqueous suspension of *Plasmopara viticola* conidia (200,000 conidia/cc) and, after 24 hours dwell time in a humidity-saturated environment, were placed back in a conditioned environment.

At the end of the incubation period (7 days), the degree of infection was evaluated according to an evaluation scale ranging from 100 (for a healthy plant) down to 0 (for a completely infected plant).

The preventive action of N-(2-methyl-5-chlorophenyl)N-methoxyacetyl-3-amino-1,3-oxazolidin-2-one against *Plasmopara viticola* on vines of cv. Dolcetto is very high in the absolute sense, since it completely (100%) inhibits the fungus infection in the very low dose of 0.0005%, both when the artificial infection is carried out after one day as well as after seven days from the treatment with the solution of said fungicide.

EXAMPLE 14

Preventive activity against *Peronospera tabacina* on tobacco

General methodology:

Cv. Burley tobacco plants grown in pots in a conditioned environment were treated by sprinkling both leaf faces with the product under examination in a hydroacetonic solution at 20% acetone (vol./vol.).

The plants were treated, respectively after 1 and 7 days, by sprinkling the lower leaf faces with an aqueous suspension of *Peronospora tabacina* Adam conidia (200,000 conidia/cc).

After 6 hours dwell time in a humidity-saturated environment, the treated plants were placed into an environment conditioned at 20° C. and 70% relative humidity for incubation of the fungus.

At the end of the incubation period (6 days), the degree of infection was evaluated according to an evaluation scale ranging from 100 (for a healthy plant) down to 0 (for a completely infected plant). Also in this type of test, compound 23 showed a decidedly superior fungicide activity.

The preventive activity against *Peronospora tabacina* of compound 23 is, moreover, extremely high in an absolute way inasmuch as, even when used in very low doses (i.e., 0.0005%), the compound is still capable of totally inhibiting the fungus infection (100% reduction) whether the artificial infection is effected 1 day or 7 days after the treatment with the compound under examination.

Like the other fungicide compositions disclosed herein, compositions comprising compound 23 as essential ingredient can also include other active substances effective in the agricultural field and compatible with compound 23, such as herbicides, fertilizers, biostimulants, other fungicides, etc.

The co-formulation of compound 23 with other so-called "coverage" fungicides is particularly useful for certain applications. Such "coverage" fungicides belong to the following classes: alkylene-bis-dithiocarbamates, copper salts or oxides, N-haloalkylthio-imides. Significant examples of such fungicides are the compounds known by the following common names: zineb, maneb, mancozeb, copper oxychloride, captan, captafol, folpet, etc.

EXAMPLE 15

By operating according to the procedure described in Example 5 and starting from the appropriate hydrazine-derivative, the compounds reported in the following Table 8 have been prepared.

TABLE 8

Compounds of formula[a]

| Compound No. | R | $R^1$ | $R^2$ | $R^3$ | n | A | $R^{4[b]}$ | m.p.[c] (°C.) | IR[d] (cm$^{-1}$) |
|---|---|---|---|---|---|---|---|---|---|
| 24 | $CH_3$ | Cl | H | H | 1 | $CH_2$ | $C_2H_5$ | oil | 1685, 1770 |
| 25 | $CH_3$ | Cl | H | H | 0 | — | 2-furyl | oil | 1650, 1760 |
| 26 | $CH_3$ | F | H | H | 1 | $CH_2$ | $OCH_3$ | 84–6 | 1690, 1780 |
| 27 | $CH_3$ | $CH_3$ | H | H | 1 | $CH_2$ | $OCH_3$ | oil | 1700, 1775 |
| 28 | Cl | Cl | H | H | 1 | $CH_2$ | $OCH_3$ | 79–81 | — |
| 29 | $CH_3$ | Cl | H | H | 0 | — |  | 116 | 1660, 1765 |

Notes to Table 8
[a]The elemental analysis of all the compounds is consistent with the assigned structure.
[b]◁ = cyclopropyl
[c]melting points have not been corrected
[d]Only the bands corresponding to ν C=O are reported.

What we claim is:

1. A fungicidally active compound which is N-(2-methyl-5-chlorophenyl)-N-methoxyacetyl-3-amino-1,3-oxazolidin-2-one.

2. A fungicide composition having, as active ingredient, a fungicidally effective amount of the compound of claim 1, together with liquid or solid inert carriers and, optionally, other agriculturally acceptable additives compatible with said active ingredient.

3. The method of combatting fungi infections of useful plants which consists in distributing on the plants or on the soil in which the plants live, as such or in the form of an agrarian formulation, a fungicidally effective amount of N-(2-methyl-5-chlorophenyl)-N-methoxyacetyl-3-amino-1,3-oxazolidin-2-one.

4. The method of combatting fungi infections of useful plants according to claim 3, characterized in that the infection is caused by Peronospora of vine (*Plasmopara viticola*).

5. The method of combatting fungi infections of useful plants according to claim 3, characterized in that the infection is caused by Peronospora of Tobacco (*Peronospora tabacina*).

* * * * *